United States Patent [19]

Vincent et al.

[11] 3,978,044

[45] Aug. 31, 1976

[54] INDAZOLE DERIVATIVES, PROCESSES FOR MAKING THE SAME AND PHARMACEUTICAL COMPOSITIONS

[75] Inventors: Michel Vincent, Bagneux; Georges Remond, Versailles, both of France

[73] Assignee: Science Union et Cie, Neuilly, France

[22] Filed: Apr. 22, 1975

[21] Appl. No.: 570,937

[30] Foreign Application Priority Data

May 2, 1974 United Kingdom............ 19239/74

[52] U.S. Cl.............. 536/117; 260/295.5 S; 260/302 H; 260/310 R; 260/310 C; 260/311; 424/273

[51] Int. Cl.²............ C07D 231/56; C07D 277/24; C07D 213/18; C13K 13/00

[58] Field of Search............ 260/310 C, 310 R, 311, 260/302 H, 295.5 S, 234 R

[56] References Cited
UNITED STATES PATENTS 3,133,081 5/1964 Lafferty et al................. 260/310 C
3,736,332 5/1973 Butula............................ 260/310 R

*Primary Examiner*—Donald B. Moyer
*Attorney, Agent, or Firm*—Behr & Woodbridge

[57] ABSTRACT

This invention relates to indazole derivatives, to processes for their preparation and to pharmaceutical compositions containing them.

More specifically this invention relates to 4, 5, 6, 7-tetrahydroindazoles bearing at the 3-position an amino substituent.

This invention also relates to processes for producing the same which include the steps of condensing a substituted cyclohexanone with a secondary amine, reacting the thus formed enamine either with an isocyanate or thiocyanate or with phosgene imonium salt and cyclizing the intermediate compound with a hydrazino derivative.

The compounds of the invention have therapeutic utility, namely as a means for controlling fertility in mammals.

7 Claims, No Drawings

INDAZOLE DERIVATIVES, PROCESSES FOR MAKING THE SAME AND PHARMACEUTICAL COMPOSITIONS

DESCRIPTION OF THE PRIOR ART

The prior are is illustrated with the following literatures:

Lednicer et al. Chem Ind 1961, 2098
Duncan et al. Proc. Soc. Exp. Biol Med 109, 163 (1962)
Duncan et al. Proc. Soc Exp Biol Med 112, 439 (1963)

SUMMARY OF THE INVENTION

This invention is concerned with new 5- substituted 3- amino tetrahydroindazoles having the formula

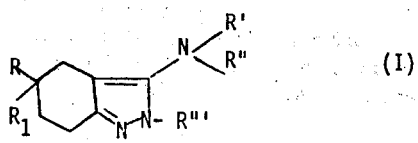

wherein

R is a hydrogen atom or a lower alkyl, phenyl, cyano or trifluoromethyl radical;

$R_1$ is a naphthyl or phenyl radical, a phenyl radical carrying one or more substituents selected from halogen atoms and trifluoromethyl, lower alkoxy, lower alkylenedioxy and phenyl radicals, or a cycloalkyl radical of the formula:

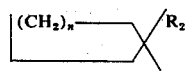

wherein $n$ is an integer from 1 to 4; or a lower alkyl radical and $R_2$ is a hydrogen atom or an alkyl radical having from 1 to 4 carbon atoms, R' is a lower alkyl, lower alkenyl or aryl radical, R'' is a lower alkyl radical or a hydrogen atom, or R' and R'' together are the alkylene chain of a nitrogenous heterocycle having from 5 to 8 ring atoms and which may further incorporate another heteroatom; and R''' is a hydrogen atom or a lower alkyl, lower alkenyl, lower alkynyl or phenyl radical, and acid addition salts thereof with mineral and organic acids.

It is further object of the invention to provide processes for producing the 3- amino 5- substituted tetrahydroindazoles having the formula I.

It is still another object of the invention to provide pharmaceutical compositions including as active ingredient at least one compound of formula I or an acid addition salt thereof with a pharmaceutical non-toxic inert carrier suitable for parenteral, oral, rectal or sublingual administration.

Another object of the invention is a method for controlling fertility in mammals which consists in administering to said animals a safe but effective amount of a compound of formula I or a salt thereof in admixture with an inert non-toxic carrier.

The compounds of formula I find a used as a means for preventing or reducing the fertility in mammals.

DESCRIPTION OF THE PREFERRED EMBODIMENTS

This invention relates to tetrahydroindazole derivatives, to processes for their preparation and to pharmaceutical compositions containing them.

The present application provides 3-amino-4,5,6,7-tetrahydroindazoles of the general formula I:

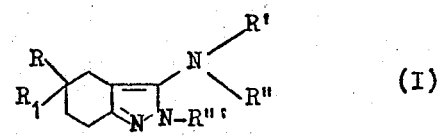

wherein

R is a hydrogen atom or a lower alkyl, phenyl, cyano or trifluoromethyl radical;

$R_1$ is a naphthyl or phenyl radical, a phenyl radical carrying one or more substituents selected from halogen atoms and trifluoromethyl, lower alkoxy, lower alkylenedioxy and phenyl radicals, or a cycloalkyl radical of the formula:

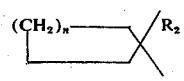

wherein $n$ is an integer from 1 to 4; or a lower alkyl radical and $R_2$ is a hydrogen atom or an alkyl radical having from 1 to 4 carbon atoms;

R' is a lower alkyl, lower alkenyl or aryl radical;

R'' is a lower alkyl radical or a hydrogen atom, or R' and R'' together are the alkylene chain of a nitrogenous heterocycle having from 5 to 8 ring atoms and which may further incorporate another heteroatom; and R''' is a hydrogen atom or a lower alkyl, lower alkenyl, lower alkynyl or phenyl radical;

and acid addition salts thereof with mineral and organic acids.

Generally speaking, the acid addition salt are formed by salification of the amino side-chain, due to the fact that the nitrogen atoms of the pyrazolic ring are insufficiently basic to be salified under normal conditions.

In this specification, the term "lower alkyl" is used to designate an alkyl group having from 1 to 6 carbon atoms in straight or branched chain which may be substituted by an hydroxyl, a lower alkoxy or a di-lower alkyl amino group. Examples of such lower alkyl groups are methyl, ethyl, isopropyl, secbutyl, neo pentyl, tertbutyl and n-hexyl.

The term 'halogen' designates preferably fluorine or chlorine. It may be also bromine or iodine.

The term "lower alkenyl" designates an alkenyl group having one or more double bonds and from 2 to 10 carbon atoms in straight or branched chain. Examples of such alkenyl groups are allyl, methallyl, isopentenyl, dimethyl allyl, butenyl, triallyl methyl, and the like.

The term "lower alkynyl" designates an alkynyl group having from 2 to 6 carbon atoms, for example ethynyl, propyn-1-yl, propyn-2-yl and methyl-1-but-2-ynyl.

The nitrogenous heterocycle having from 5 to 8 ring atoms may be pyrrolidine, piperidine, or hexamethylene imine. It may also include an additional heteroatom, for example, a nitrogen atom, a sulfur atom or an oxygen atom. Examples of such heterocycles are oxazolidine, morpholine, thiazolidine, thiamorpholine, piperazine, and homo-morpholine. These heterocycles may carry also one or more alkyl groups, for example 2,5-dimethyl piperazine.

The term "aryl" is used to designate a phenyl radical, a phenyl radical which carries one or more substituents selected from halogen atoms, and lower alkoxy, lower alkyl, lower alkylthio, lower acylamino, trifluoromethyl, trifluoromethylthio, trifluoromethoxy and alkylenedioxy groups or an α- or β-naphthyl, biphenylyl or halobiphenylyl radical.

The acids used to form acid addition salts are preferably those which are therapeutically compatible, such as mineral acids, for example hydrochloric acid, hydrobromic acid, phosphoric acid, nitric acid and sulphuric acid; or organic acids, for example acetic acid, benzoic acid, salicylic acid, trimethoxy-benzoic acid, naphthoic acid, furan acetic acid, 5-thiazolyl carboxylic acid, nicotinic acid, isethionic acid, methansulphonic acid, toluenesulphonic acid and phenylsulphonic acid; or organo-phosphoric acids, for example glucose-1-phosphoric acid, glucose-1,6-di phosphoric acid and ethyl phosphoric acid.

When the molecule includes an asymmetric carbon atom, the compounds of the invention may exist in an optically active form. They may be resolved during their synthesis or after synthesis. They may be also obtained using a starting material which has been previously resolved.

The present invention also provides a process for producing the compounds of general formula I which comprises condensing a substituted cyclohexanone of the formula III:

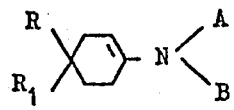

in which R and R₁ have the meanings given above with a secondary amine of the formula IV:

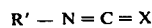

wherein A and B, which are the same or different, are each a lower alkyl radical or a phenyl radical or together are the alkylene chain of a nitrogenous heterocycle having from 4 to 7 ring atoms and which may incorporate a further heteroatom, to obtain a cyclohexylenamine of the formula V:

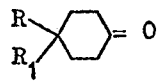

in which R, R₁, A and B have the meanings given above, reacting the latter either with an isocyanate or an isothiocyanate of the formula VI:

in which X is an oxygen or a sulphur atom and R' has the meanings given above, in the presence or in the absence of a Lewis acid as catalyst to obtain a cyclohexyl carboxamide of the formula VII:

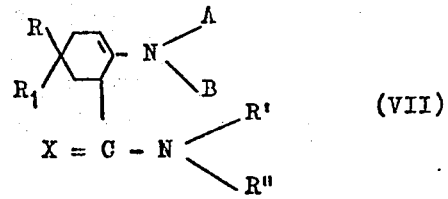

in which R, R₁, and R', A and B have the meanings given above and R'' is a hydrogen atom, or with a carbamoyl halide of the formula

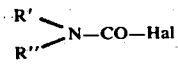

in which Hal is a halogen atom and R' and R'' have the meanings given above to produce a cyclohexyl carboxamide of the formula VII':

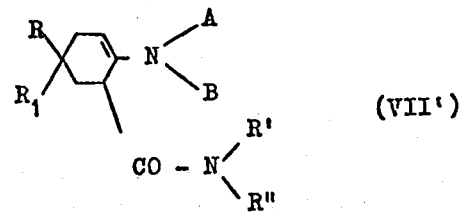

in which A, B, R, R', R'' and R₁ have the meanings given above, hydrolysing the enamine group in an acidic medium to obtain an α-keto carboxamide of the formula VIII:

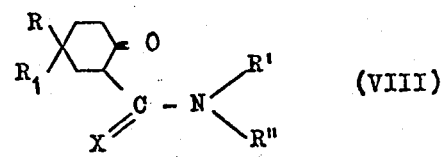

in which
R', R and R₁ have the meanings given above, and
R'' represents a hydrogen atom when X is a sulphur atom or
R'' represents a hydrogen atom or a lower alkyl radical or forms with R' the alkylene chain of a nitrogenous heterocycle having from 5 to 8 ring atoms when X is an oxygen atom, and cyclising the latter by means of an hydrazino derivative of the formula:

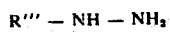

in which R''' has the meanings given above, in the presence of an acid to produce a tetrahydroindazole of formula I:

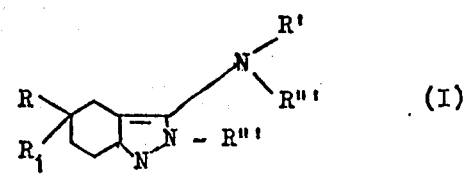

in which substituents R, $R_1$, R', R'' and R''' have the meanings given above which may, if desired, be salified by adding a mineral or organic acid or, when the molecule includes an asymmetric carbon atom, may be resolved by salifying it with an optically-active carboxylic, sulphonic or phosphoric acid.

The present invention also provides a process for producing the compounds of formula I in which a hydrazino derivative of the formula:

R''' — NH — NH$_2$ is reacted with a cyclohexyl carboxamide of the formula VII or VII' in order to obtain a hydrazone of the formula IX:

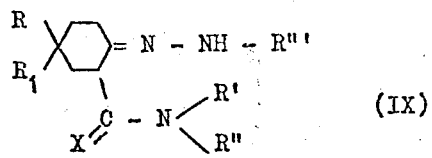

in which R, $R_1$, X, R', R'' and R''' have the meanings given above, which is cyclised in an acidic medium into a tetrahydroindazol of the formula I.

According to preferred features of the invention the condensation of the substituted cyclohexanone with a secondary amine of the formula IV is performed in the presence of an acidic agent such as acetic acid, oxalic acid, p. toluenesulphonic acid or boron trifluoride.

the reaction of the enamine of the formula V with an isocyanate or thio cyanate is performed in an inert solvent such as a halogenated alkane, a lower cyclo alkane, a linear or cyclic alkyl ether, or an aromatic hydrocarbon, by heating at a temperature comprised between 50° and 150°.

the reaction of the enamine of the formula V with an isocyanate or a thiocyanate is performed in the presence of a lewis acid such as zinc chloride, aluminium chloride or boron trifluoride.

the hydrolysis of the compounds of the general formula VII or VII' is performed by means of a mineral or organic acid such as hydrochloric acid, perchloric acid or acetic acid or by exchange of function with a carbonylated derivative such as pyruvic acid, glyoxylic acid or α ketolevulinic acid.

the cyclisation of the compounds of the formula VIII is performed in the presence of an acid such as a mineral acid for example hydrochloric acid or an organic carboxylic or sulphonic acid for example, formic acid, acetic acid, methanesulphonic acid or p. toluene sulphonic acid.

The present invention further provides a process for producing the compounds of formula I in which a hydrazino derivative of the formula:

R''' — NH — NH$_2$ is reacted with a cyclohexanone of the formula III and the resulting hydrazone of the formula X:

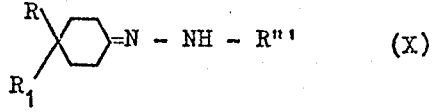

in which R, $R_1$ and R''' have the meanings given above, is condensed with a phosgene imonium chloride of the formula XI:

in which R' and R'' have the meanings give above, and cyclised by heating to obtain a tetrahydroindazole of the formula I.

The phosgene imonium salts of formula XI can be prepared according to the method described by H. G. Viehe and Z. Janousek, Ang. Chemie 83 (1973) 581.

The compounds of general formula I have interesting pharmacological properties. They are endowed with antifertility activity which makes them useful for preventing or inhibiting pregnancy in mammals.

This antifertility activity can be illustrated by determining the number of implantation sites in mice receiving an effective doses of the tested compound, after cohabitation with individual males.

The compounds of formula I have a very low toxicity, possess a broad margin of safety, and therefore allow prolonged administration without undesired side-effects.

The present invention therefore also provides pharmaceutical compositions including as active ingredient one or more compounds of general formula I in admixture or conjunction with a non-toxic inert pharmaceutical carrier, especially for preventing pregnancy especially in cattle.

For this therapeutic use the pharmaceutical compositions are those suitable for being administered by a parenteral, oral, rectal or sublingual way, more particularly in the form of tablets, coated tablets, capsules, ampuls, phials, multi-dosis flasks, granulates, suppositories or sublingual tablets.

When administered to cattle it may also be advantageous to incorporate the active ingredient to the feed, by mixing said active ingredient to premixes or to granulates for animal feeding.

The posology may vary depending to the subject to be treated. It ranges from 1 to 100 mg/kg per day and more preferably from 5 to 25mg/kg.

The present invention also provides the intermediate compounds useful for producing the compounds of formula I, namely:

1. the enamines of formula V:

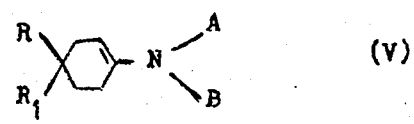

wherein A, B, R and $R_1$ have the meanings give above, and especially 4-isobutyl 1-morpholyl cyclohex-1-ene and 4-cyclohexyl 1-morpholyl cyclohex-1-ene;

2. the carboxamides of formula VII:

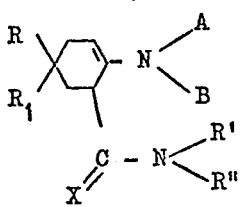

wherein R, R₁, A, B, R', R'' and X have the meanings given above, and the carboxamides of formula VII':

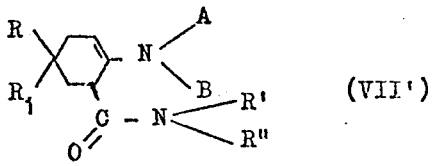

in which the substituents R, R₁, R', R'', A and B have the meanings given above, and more especially 4-isobutyl 2-methylthiocarbamoyl 1-morpholyl cyclohex-1-ene, 4-isobutyl 2-phenylthiocarbamoyl 1-morpholyl cyclohex-1-ene, 4-cyclohexyl 2-allylthiocarbamoyl 1-morpholyl cyclohex-1-ene, and 4-cyclohexyl 2-phenylthiocarbamoyl 1-morpholyl cyclohex-1-ene;

3. the α-keto carboxamides of formula VIII:

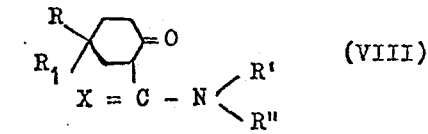

wherein X, R, R₁, R' and R'' have the meanings given above, and more especially 4-isobutyl 2-methylthiocarbamoyl cyclohexanone-1,
4-isobutyl 2-phenylthiocarbamoyl cyclohexanone-1,
4-cyclohexyl 2-allylthiocarbamoyl cyclohexanone-1,
4-cyclohexyl 2-methylthiocarbamoyl cyclohexanone-1, and
4-cyclohexyl 2-phenylthiocarbamoyl cyclohexanone-1; and 4. the hydrazones of formula IX:

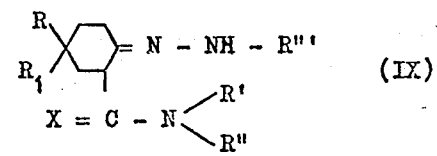

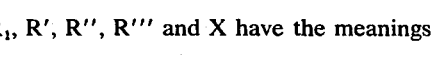

wherein R, R₁, R', R'', R''' and X have the meanings given above.

The cyclohexanones of general formula III, used as starting materials are known compounds. They may be obtained according to the processes described in British Pat. No. 1,329,462.

The following Examples illustrate the invention.

EXAMPLE 1

5-cyclohexyl-3-methylamino-2-methyl-4,5,6,7-tetrahydroindazole and its acid tartarate

Step A 4-cyclohexyl-1-morpholyl-cyclohex-1-ene 54 g of 4-cyclohexanone are dissolved in 90 ml benzene and 39 ml morpholine are added to the fresh solution, then a few crystals of p-toluene sulphonic acid. The whole is heated under reflux for 3 days while distilling off the water-benzene mixture. The remaining benzenic solution is evaporated to dryness under reduced pressure. The dry residue weighs 76.8 g and the raw product shows a melting point of 88°–90°. The raw enamine is ground, then dried in vacuo to constant weight. 74.3 g of 4-cyclohexyl-1-morpholyl-cyclohex-1-ene are recovered and used without further purification for the next step of the synthesis. The yield amounts to 99%.

Step B 4-cyclohexyl-2-methylthiocarbamoyl-1-morpholyl-cyclohex-1-ene

In a three-neck flask there are introduced successively 2.04 g of methyl isothiocyanate, 20 ml heptane and, over the course of 5 minutes, a solution of 7.1 g 4-cyclohexyl-1-morpholyl-cyclohex-1-ene in 80 ml heptane and the reaction mixture is kept under vigourous stirring for 18 hours at room temperature.

During this period, a slight reddish precipitate appears and is maintained in suspension. The mixture is heated to reflux for 6 hours and allowed to stand over night. The heptanic phase is separated, filtered and concentrated under reduced pressure. 5.48 g of a yellowish oil product are recovered. Moreover, the solid matter separated by filtration weighs 3.6 g. The two fractions are united, dissolved in the minimal amount of hot isopropanol. In the cold, 4-cyclohexyl 2-methylthiocarbamoyl 1-morpholyl cyclohex-1 ene crystallyses. The crystals are separated, dried, washed and dried again.

Step B 4-cyclohexyl 2-methylthiocarbamoyl 1-morpholyl cyclohex-1 ene

It may also be produced according to the following procedure. 62.4 g of 4-cyclohexyl 1-morpholyl cyclohex-1 ene are dissolved in 600 ml chloroform and 18.2 g of methyl isothiocyanate are added thereto. The whole mixture is transfered to a well-closed flask and heated at 70° for six hours.

The orange coloured solution is concentrated off under vaccuum and 85.2 g of a dry residue are recovered as yellow crystalls.

The raw product is further purified by recrystallization from hot isopropanol. After cooling overnight in the refrigerator, the crystalls are separated, dried, rinced with a little isopropanol then with ethyl ether and dried again at 40°. Finally, 39 g of 4-cyclohexyl 2-methylthiocarbamoyl 1-morpholyl cyclohex-1 ene are obtained, melting at 167°. The product is identical to that obtained according to procedure of Step B. For analytical purpose a sample is crystallized from ethanol. The melting point is increased to 174°–175°.

Step C 5-cyclohexyl 3-methylamino 2-methyl 4,5,6,7 tetrahydro indazole

In a three-neck flask incorporating a mechanical stirring device and a funnel, 9.67 g of 4-cyclohexyl 2-methylthiocarbamoyl 1-morpholyl cyclohex-1 ene, 3.6 g acetic acid and 60 ml ethanol are introduced. The so-formed suspension is kept under stirring for 15 minutes.

Through the funnel a solution of 1.52 g of methylhydrazine in 60 ml ethanol is added dropwise while avoiding the inner temperature reaches 30°. The yellow gold solution of the thus-formed methyl hydrazone is then heated to reflux for 3 hours until the evolution of sulphric acid has ceased.

The solvent is thereafter evaporated off and 15.1 g of dry residue are recovered. The dry residue is taken up in 50 ml ether. The insoluble matter is essentially the morpholine acetate and is separated by filtration. The filtrate is concentrated off giving an oily residue weighing 10.5 g.

It is further purified by taking it up with 50 ml N hydrochloric acid solution and 50 ml ether. The aqueous phase is decanted, and washed three times with ether. The aqueous solution of the hydrochloride is then made basic by adding potassium carbonate.

The free base precipitates. The precipitate is separated by filtration and extracted three times with ether. The etherous solutions are united, dried on magnesium sulphate, filtered and evaporated off under vaccuum.

A crystalline residue weighing 5.8 g is recovered and recrystallized from hot heptane. The crystalls are separated, dried and rinced with heptane before thoroughly drying at 45°. 3.8 g of 5-cyclohexyl 3-methylamino 2-methyl 4,5,6,7-tetrahydro indazole are thus recovered giving a yield of 51%. 5-cyclohexyl 3-methylamino 2-methyl 4,5,6,7-tetrahydroindazole melts at 127° C.

Step D 5-cyclohexyl 3-methylamino 2-methyl 4,5,6,7-tetrahydro indazole, acid d-tartarate 3.75 g of 5-cyclohexyl 3-methylamino 2-methyl 4,5,6,7-tetrahydroindazole obtained at step C are suspended in 90 ml ether. A solution of 2.4 g of d-tartaric acid in 20 ml ethanol is added hereto and it appears immediately a reddish precipitate. After standing one hour, the insoluble matter is sucction-filtered and the filtrate is concentrated on the water-bath until the mixture begins to crystallize. The crystallized mixture is kept at room temperature over night, then filtered. The crystals are dried, rinced with ether and dried again.

4.8 g of acid d-tartarate are thus recovered melting at 152° i.e. a yield of 40.3%.

The acid d-tartarate is soluble in water giving a slightly acid solution (pH = 5).

EXAMPLE 2

5-cyclohexyl 3-methylamino 4,5,6,7-tetrahydroindazole and its hydrochloric acid addition salt Using the same procedure as at step C of example I, but starting of 6.44 g of 4-cyclohexyl 2-methylthiocar-bamoyl 1-morpholino cyclohex-1 ene dissolved in 40 ml ethanol and 2.4 g acetic acid and 1.1 g hydrazine hydrate in 40 ml ethanol, raw 5-cyclohexyl 3-methylamino 4,5,6,7-tetrahydroindazole is recovered. The raw product is suspended in 100 ml ether and 100 ml N soltuion of hydrochloric acid are added. The hydrochloride precipitates and is suction-filtered, then dried, rinced with water then with ether and further dried. 1.7 g of 5-cyclohexyl 3-methylamino 4,5,6,7-tetrahydroindazole hydrochloride are thus obtained, melting at 177 then 240° then 270°.

The ethereous mother liquors are separated and the acidic aqueous phase extracted three times with ether. The ethereous solutions are united and made basic with potassium carbonate. The free base precipitates as an oily product, is isolated by decantation then extracted with ether. The ethereous solution dried on sodium sulphate is filtered then evaporated to dryness, under vaccuum.

2.8 g of 5-cyclohexyl 3-methylamino 4,5,6,7-tetrahydroindazole are thus obtained and are further purified by converting them anew into the hydrochloride. A second crop of hydrochloride weighing 2 g is thus obtained. The compound melts at 174°–178°.

5-cyclohexyl 3-methylamino 4,5,6,7-tetrahydroindazole occurs as white-yellow crystalls soluble in water.

EXAMPLE 3

5-cyclohexyl 3-methylamino 4,5,6,7-tetrahydroindazole

The compound of example 2 may also be obtained in the following manner.

Step A 4-cyclohexyl 2-methylthiocarbamoyl cyclohexanone 1 g of 4-cyclohexyl 2-methylthiocarbamoyl 1-morpholyl cyclohex-1 ene is dissolved in 20 ml ethanol at room temperature. To this solution 2 ml 4 N hydrochloric acid solution are added and the mixture becomes pale yellow. The reaction mixture is kept under stirring for ½ hour. 60 ml water are then added and a brownish-red precipitate appears. It is sucction-filtered, washed with water and further taken up in benzene until complete solution. The benzenic solution is dried, filtered and evaporated to dryness. The dry residue is further washed with water then taken up with benzene. After distillation of the solvent 0.7 g of 4-cyclohexyl 2-methyl thio carbamoyl cyclohexanone are thus obtained which is used as such for the next step of the synthesis.

Step B 5-cyclohexyl 3-methylamino 4,5,6,7-tetrahydro indazole 0.7 g of 4-cyclohexyl 2-methylthiocarbamoyl cyclohexanone dissolved in 30 ml ethanol are added with 0.15 g hydrazine hydrate. The mixture is heated to reflux for 30 mn until the evolution of sulphydric gas has ceased. 0.3 ml acetic acid are thereafter added and the whole is refluxed for 3 hours. The mixture is evaporated off giving a yellow liquid as residue. The residue is taken up with ether; the organic solution is washed with a saturated aqueous solution of sodium bicarbonate then with water until the washings are neutral, finally dried and evaporated off. 0.6 g of 5-cyclohexyl 3-methylamino 4,5,6,7-tetrahydroindazole are thus recovered and recrystallized from the minimum amount of isopropanol.

EXAMPLE 4

5-cyclohexyl 3-phenylamino 4,5,6,7-tetrahydroindazole

Using the procedure of example 1 and starting from 9.2 g of 4-cyclohexyl 1-morpholyl cyclohex-1 ene and from 5 g phenyl isothiocyanate 7.8 g of 4-cyclohexyl 2-phenylthiocarbamoyl 1-morpholyl cyclohex-1 ene are obtained, melting at 143°. Acid hydrolysis of 7 g of 4-cyclohexyl 2-phenylthiocarbamoyl 1-morpholyl cyclohex-1 ene gives 4.5 g of 4-cyclohexyl 2-phenylthiocarbamoyl cyclohexanone which melts at 150°.

Using the procedure of example 3, step B, starting from 6.9 g of 4-cyclohexyl 2-phenylthiocarbamoyl cyclohexanone and from 1.17 g hydrazine hydrate 3.1 g of a first crop of 5-cyclohexyl 3-phenylamino 4,5,6,7-tetrahydroindazole is obtained which melts at 167° after recrystallization from methanol.

EXAMPLE 5

5-cyclohexyl 3-phenylamino 2-methyl 4,5,6,7-tetrahydroindazole

Using the same procedure as at step C of example 1 and starting from 6.9 g of 4-cyclohexyl 2-phenylthiocarbamoyl cyclohexanone and 1.1 g methyl hydrazine, 5.8 g of 5-cyclohexyl 3-phenylamino 2-methyl 4,5,6,7-tetrahydroindazole are recovered. The pure product melts at 166°–167° after recrystallization from methanol.

In a similar manner starting from 6.9 g of 4-cyclohexyl 2-phenylthiocarbamoyl cyclohexanone and from 1.68 g propargylhydrazine, 4.10 g of 5-cyclohexyl 3-phenylamino 2-propynyl 4,5,6,7-tetrahydroindazole are obtained. In a similar manner starting from 6.9 g 4-cyclohexyl 2-phenylthiocarbamoyl cyclohexanone and 1.70 g allylhydrazine, 5.4 g of 5-cyclohexyl 3-phenylamino 2-propenyl 4,5,6,7-tetrahydro indazole are obtained.

EXAMPLE 6

5-isobutyl 3-phenylamino 4,5,6,7-tetrahydroindazole

Using the same procedure as in example 1 and starting from 46.2 g of 4-isobutyl cyclohexanone the following compounds have been obtained:

4-isobutyl 1-morpholyl cyclohex-1-ene ($Eb_{0.05}$ = 113°–115°), 4-isobutyl 2-phenylthiocarbamoyl 1-morpholyl cyclohex-1-ene melting at 134°–135° (methanol), 4-isobutyl 2-phenylthiocarbamoyl cyclohexanone melting at 121°–122°, 5-isobutyl 3-phenylamino 4,5,6,7-tetrahydroindazole (MP 110 then 126°–128°).

EXAMPLE 7

5-isobutyl 3-phenylamino 2-methyl 4,5,6,7-tetrahydroindazole

Using the same procedure as in example 3, step C, and starting from 10 g 4-isobutyl 2-phenyl thiocarbamoyl cyclohexanone and from 1.74 g methyl hydrazine 20.1 g of 5-isobutyl 3-phenylamino 2-methyl 4,5,6,7-tetrahydroindazole is formed which after recrystallization from aqueous methanol then from hexane melts at 130°. The yield amounts 6.8 g i.e. 70%.

EXAMPLE 8

5-cyclohexyl 3-allylamino 4,5,6,7-tetrahydroindazole

Using the same procedure as in example I and starting from 9.2 g of 4-cyclohexyl 1-morpholyl cyclohex-1 ene (obtained at step B of example 1) and 3.66 g of allyl isothiocyanate there are obtained successively:

4-cyclohexyl 2-allylthiocarbamoyl 1-morpholyl cyclohex-1 ene liquid 5-cyclohexyl 3-allylamino 4,5,6,7-tetrahydroindazole (MP = 163° after recrystallization from ethanol).

EXAMPLE 9

5-cyclohexyl 3-allylamino 2-methyl 4,5,6,7-tetrahydro indazole

Using the procedure of step B of example 8 and starting from 4.25 g of 4-cyclohexyl 2-allylthiocarbamoyl 1-morpholyl cyclohex-1-ene and 1.44 g of methyl hydrazine, 5.7 g of raw 5-cyclohexyl 3-allylamino 2-methyl 4,5,6,7-tetrahydroindazole are obtained. For analytical purposes the product is purified by conversion as its hydrochloride. The latter recrystallized from a mixture of ether and isopropanol, melts above 260° (with sublimation).

After treatment with a base, 5-cyclohexyl 3-allylamino 2-methyl 4,5,6,7-tetrahydroindazole is obtained from the hydrochloride and melts at 168° (from methanol).

EXAMPLE 10

5-cyano 5-phenyl 3-ethylamino 2-phenyl 4,5,6,7-tetrahydroindazole

Step A sodium 4-phenyl 4-cyano 2-methoxycarbonyl cyclohex-1 enolate

A fresh solution of sodium methylate has been prepared by reacting 30.4 g of sodium cuttings with 432 ml methanol while cooling the mixture. After the reaction has ceased, 150 g benzyl cyanide is added dropwise under stirring then 223.8 g freshly distillated methyl acrylate. The whole mixture is heated to reflux for 3 hours and thereafter kept aside overnight. The thus appeared precipitate is separated by filtration, washed several times with ether and dried at about 50° giving 179.7 g of sodium 4-cyano 4-phenyl 2-methoxycarbonyl cyclohex-1 enolate.

The compound titrating 99% of pure product is used as such for the next step of the synthesis.

Step B 4-phenyl 4-cyanocylohexanone

In a flask they were introduced successively under nitrogen atmosphere 179.7 g of sodium 4-cyano 4-phenyl 2-methoxy carbonyl cyclohex-1-enolate, 450 ml water, 450 ml acetic acid then 180 ml hydrochloric acid. It appears a milky suspension which is heated to reflux under stirring. After 5 hours heating the evolution of carbon dioxide has ceased and a green homogeneous solution is obtained. After reverting to room temperature this solution is carefully neutralized by adding a 5 N solution of sodium hydroxide while maintaining the inner temperature at about 20° by means of a iced water bath.

4-phenyl 4-cyano cyclohexanone precipitates and is separated by filtration dried and washed with water. It is further taken up with benzene until completely dissolved. The benzenic solution is decanted, washed with water, dried on sodium sulphate, filtered and evaporated off 101.3 g of 4-phenyl 4-cyano cyclohexanone are thus recovered which are recrystallized from cyclohexane giving a first crop of 86.4 g. The yield amounts to 67.5%. 4-phenyl 4-cyano cyclohexanone melts at 115°C.

Step C

4-phenyl 4-cyano 1-pyrrolidine cyclohex-1 ene

Using the procedure of step A at example 1 and starting from 79.6 g of 4-phenyl 4-cyanocyclohexanone and 56.8 g pyrrolidine there is obtained with a theoretical yield 4-cyano 4-phenyl 1-pyrrolidino cyclohex-1-ene.

Step D

4-phenyl 4-cyano 2-methylthiocarbamoyl 1-pyrrolidino cyclohex-1-ene

Using the procedure of step B at example 10 and starting from 126.4 g 4-phenyl 4-cyano 1-pyrrolidino cyclohex-1 ene and 40 g ethyl isothiocyanate, 107.25 g of 4-phenyl 4-cyano 2-ethylthiocarbamoyl 1-pyrrolidino cyclohex-1 ene are obtained after the usual purifications.

Step E

5-phenyl 5-cyano 3-ethylamino 2-phenyl 4,5,6,7-tetrahydroindazole

Using the procedure of step C at example I and starting from 97.5 g 4-phenyl 4-cyano 2-methylthiocarbamoyl 1-pyrrolidino cyclohex-1 ene, 18 g acetic acid and 18.5 g phenyl hydrazine, 49.78 g of 5-phenyl 5-cyano 3-ethylamino 2-phenyl 4,5,6,7-tetrahydroindazole are obtained i.e. a yield of 61%.

EXAMPLE XI

Pharmaceutical study of the compounds of general formula I.

The compounds of general formula I have been tested according to the anti-fertility test method described by Duncan, G. W. et al. Proceed. Soc Exp. Biol. Med 112 (1963) 439–442.

The test was carried out as follows:

Four female mice are housed together and given the first dose of test drug (25mg/kg, p.o.) on Monday morning. Monday afternoon pairs of females are placed in cages with single males where they are left until Friday afternoon whereupon the females are returned four to a cage to their original cages. The females are dosed in the morning Tuesday through Saturday. Copulation plugs are noted at each day's dosing. The animals are kept at 70°–72° F during mating and for one week thereafter when the females are sacrificed and their uteri examined for evidence of pregnancy. All females must be free of embryos to indicate antifertility effect. The dosing schedule more than covers one estrous cycle and since dosing is accomplished before, during, and after copulation, all of the possible mechanisms of action are pretty well covered.

The compounds were tested at dosis ranging from 5 to 25mg/kg. Complete inhibition of the implantation sites was obtained at the highest dosages.

Acute toxicity

The compounds of general formula have been tested for acute toxicity on batches of mice weighing from 20 to 22 g. Increasing dosis have been administered by oral way. The animals are kept under survey for seven days and death is noticed.

Up to the dosis of 2g/kg no lethality at all was observed.

What we claim is:

1. A 3-amino 4, 5, 6, 7 - tetrahydroindazoles of the formula

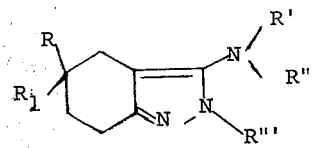

wherein R is hydrogen and $R_1$ is cycloalkyl of the formula

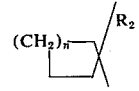

wherein $n$ is an integer of 1 to 4 and $R_2$ is hydrogen, R' is phenyl, R'' is hydrogen or lower alkyl and R''' is selected from the group consisting of hydrogen, lower alkyl, lower alkenyl, lower alkynyl and phenyl wherein lower alkyl contains 1 – 6 carbon atoms, lower alkenyl contains 2 – 10 carbon atoms and lower alkynyl contains 2 – 6 carbon atoms and the therapeutically compatible mineral or organic acid addition salts.

2. 5-cyclohexyl 3-methylamino 4, 5, 6, 7-tetrahydro indazole and its hydrochloride, according to claim 1.

3. 5-cyclohexyl 3-phenylamino 2-methyl 4, 5, 6, 7-tetrahydro indazole, according to claim 1.

4. 5-cyclohexyl 3-phenylamino 2-(propynyl-1') 4, 5, 6, 7-tetrahydro indazole, according to claim 1.

5. 5-cyclohexyl 3-phenylamino 2-(propenyl-1') 4, 5, 6, 7-tetrahydro indazole, according to claim 1.

6. 5-cyclohexyl 3-allylamino 4, 5, 6, 7-tetrahydro indazole, according to claim 1.

7. An acid addition salt of claim 1 wherein the acids are selected from the group consisting of hydrochloric, hydrobromic, phosphoric, nitric, sulphuric, acetic, benzoic, salicyclic, trimethoxy-benzoic, naphthoic, furan acetic, 5-thiazolyl carboxylic, nicotinic, isothionic methansulphonic, toluenesulphonic, phenyl-sulphonic, glucose-1-phosphoric, glucose-1, 6-di phosphoric and ethyl phosphoric acids.

* * * * *